(12) United States Patent
Jang et al.

(10) Patent No.: US 10,288,533 B2
(45) Date of Patent: May 14, 2019

(54) SAMPLE COLLECTION APPARATUS

(71) Applicant: KOREA INSTITUTE OF OCEAN SCIENCE TECHNOLOGY, Gyeonggi-do (KR)

(72) Inventors: Seok Jang, Gyeonggi-do (KR); Dong Hyeok Shin, Incheon (KR); Young Sang Eo, Gyeonggi-do (KR)

(73) Assignee: KOREA INSTITUTE OF OCEAN SCIENCE TECHNOLOGY, Gyeonggi-Do (KR)

( * ) Notice: Subject to any disclaimer, the term of this patent is extended or adjusted under 35 U.S.C. 154(b) by 21 days.

(21) Appl. No.: 15/571,656

(22) PCT Filed: Apr. 14, 2016

(86) PCT No.: PCT/KR2016/003873
§ 371 (c)(1),
(2) Date: Nov. 3, 2017

(87) PCT Pub. No.: WO2016/178479
PCT Pub. Date: Nov. 10, 2016

(65) Prior Publication Data
US 2018/0143104 A1   May 24, 2018

(30) Foreign Application Priority Data
May 4, 2015   (KR) .................. 10-2015-0062701

(51) Int. Cl.
*E02D 1/04* (2006.01)
*G01N 1/12* (2006.01)
(Continued)

(52) U.S. Cl.
CPC .............. *G01N 1/12* (2013.01); *G01N 1/04* (2013.01); *G01N 1/08* (2013.01); *B66C 3/06* (2013.01);
(Continued)

(58) Field of Classification Search
CPC ..... B66C 3/06; B66C 3/02; E02D 1/04; E02F 3/47; E21B 49/025; E21B 49/02
See application file for complete search history.

(56) References Cited

U.S. PATENT DOCUMENTS

| 321,159 A | * | 6/1885 | Thompson | ................ B66C 3/12 37/186 |
| 400,936 A | * | 4/1889 | Morris | ..................... B66C 3/12 37/186 |

(Continued)

FOREIGN PATENT DOCUMENTS

| JP | 3188856 U | 2/2014 |
| KR | 101056355 B1 | 8/2011 |

(Continued)

OTHER PUBLICATIONS

International Search Report issued in PCT/KR2016/003873 dated Jul. 14, 2016, 4 pages.

*Primary Examiner* — David A Rogers
(74) *Attorney, Agent, or Firm* — RatnerPrestia

(57) ABSTRACT

Disclosed is a sample collection apparatus. The sample collection apparatus relates to a sample collection apparatus configured to be capable of stably collecting sediment from a seabed without disturbing the same and to be capable of easily separating and transporting a box itself containing a sample from the sample collection apparatus. Briefly, the sample collection apparatus includes a frame section, a vertical operation section, and a rotary operation section.

19 Claims, 10 Drawing Sheets

(51) Int. Cl.
  *G01N 1/04* (2006.01)
  *G01N 1/08* (2006.01)
  *E02F 3/47* (2006.01)
  *E21B 49/02* (2006.01)
  *B66C 3/06* (2006.01)

(52) U.S. Cl.
  CPC .............. *E02D 1/04* (2013.01); *E02F 3/47* (2013.01); *E21B 49/02* (2013.01); *E21B 49/025* (2013.01)

(56) References Cited

U.S. PATENT DOCUMENTS

| | | | | |
|---|---|---|---|---|
| 611,357 A * | 9/1898 | Dembinski | ......... | B65D 90/623 294/68.24 |
| 1,477,679 A * | 12/1923 | Woolley | ............ | B66C 3/08 37/184 |
| 2,136,890 A * | 11/1938 | Roberts | ............ | B66C 3/16 294/68.23 |
| 2,242,940 A * | 5/1941 | Caoli | .............. | B66C 3/06 37/184 |
| 3,036,393 A * | 5/1962 | Baird, Jr. | ............ | B66C 3/06 294/68.23 |
| 3,357,506 A * | 12/1967 | De Bosredon | .... | E02F 3/47 175/99 |
| 3,693,274 A * | 9/1972 | Piccagli | ........... | B66C 3/16 37/187 |
| 3,762,078 A * | 10/1973 | Wetherbee | ........ | E02F 3/4131 175/253 |
| 3,934,917 A * | 1/1976 | Paxton | ............ | B66C 3/06 294/68.23 |
| 3,949,497 A * | 4/1976 | Crump | ............ | E02F 3/4131 37/340 |
| 3,996,678 A * | 12/1976 | Amann | ............ | E02D 1/04 37/340 |
| 4,043,580 A * | 8/1977 | Thaule | ........... | B66C 3/06 294/68.23 |
| 4,116,069 A * | 9/1978 | Lezgintsev | ........ | E02F 3/4131 37/186 |
| 4,129,329 A * | 12/1978 | Longo | ............ | B66C 3/16 294/68.23 |
| 4,174,131 A * | 11/1979 | Gregg | ........... | B66C 3/06 294/68.23 |
| 4,328,987 A * | 5/1982 | Zoudlik | ............ | B66C 3/12 294/111 |
| 4,373,278 A * | 2/1983 | Myrick | ............ | E02F 3/4131 37/184 |
| 4,381,872 A * | 5/1983 | Hahn | ............... | B66C 3/06 294/111 |
| 4,908,966 A * | 3/1990 | Phillips | ............ | B66C 3/02 24/DIG. 32 |
| 5,199,194 A * | 4/1993 | Scott | ............... | E02F 3/47 294/68.23 |
| 5,443,294 A * | 8/1995 | Prinz | ............... | B66C 3/06 294/68.23 |
| 5,540,005 A * | 7/1996 | Lynch | ............ | E02F 3/4131 294/68.23 |
| 5,649,729 A * | 7/1997 | Peterson | ........... | B66C 3/06 254/337 |
| 5,836,089 A * | 11/1998 | Lipsker | ............ | B66C 3/02 37/186 |
| 6,463,801 B1 * | 10/2002 | Young | ............. | E02D 1/04 73/170.32 |
| 6,684,536 B2 * | 2/2004 | Anderson | .......... | A01C 11/003 37/340 |
| 7,607,643 B1 * | 10/2009 | Box | .................. | B66D 3/04 254/323 |
| 8,908,476 B2 * | 12/2014 | Chun | .............. | B63G 8/001 114/312 |
| 9,416,654 B2 * | 8/2016 | Lee | ................. | E21B 49/02 |
| 2003/0019131 A1 * | 1/2003 | Anderson | .......... | A01C 11/003 37/184 |
| 2007/0246620 A1 * | 10/2007 | Looijen | ............ | E21B 41/08 248/188.2 |
| 2010/0017035 A1 * | 1/2010 | Van Den Berg | ...... | A01K 1/01 700/259 |
| 2012/0204781 A1 * | 8/2012 | Chun | .............. | B63G 8/001 114/312 |
| 2014/0144255 A1 * | 5/2014 | Lee | ................. | E21B 49/02 73/864.65 |

FOREIGN PATENT DOCUMENTS

| | | |
|---|---|---|
| KR | 1020110088461 A | 8/2011 |
| KR | 101277324 B1 | 6/2013 |
| KR | 101361143 B1 | 2/2014 |

\* cited by examiner

SAMPLE COLLECTION APPARATUS

CROSS REFERENCE TO RELATED APPLICATIONS

This application is the U.S. National Phase Application of PCT/KR2016/003873, filed Apr. 14, 2016, which claims priority to Korean Patent Application No. 10-2015-0062701, filed May 4, 2015, the contents of such applications being incorporated by reference herein.

BACKGROUND OF THE INVENTION

Field of the Invention

The present disclosure relates to a sample collection apparatus, and more particularly, to a sample collection apparatus that is configured such that the sediment of a seabed can be stably collected without disturbing the same and a box itself containing the sample can be easily separated from the collection apparatus so as to be transported.

Description of the Prior Art

In recent years, a box-type sample collection apparatus has been used for the purpose of collecting sediment as well as manganese nodules from a seabed without disturbing the same and reducing a sample collection time.

As a prior art of such a box-type sample collection apparatus, a complex sample collection apparatus is disclosed in Korean Patent No. 10-1277324 (published on Jun. 20, 2013). The complex sample collection apparatus includes: a main sample collection unit having a predetermined weight to sink to the seabed and to dig into the seabed topography, thereby collecting a sample containing sediment; one or more subordinate sample collection units disposed on a side of the main sample collection unit and configured to recognize arrival at the seabed and to scrape the surface of the seabed topography, thereby collecting a predetermined amount of the sample; and an image acquisition unit installed in the main sample collection unit and configured to acquire an image of the seabed topography.

From this complex sample collection apparatus, it has been expected that a sample, such as manganese nodules, can be collected by simultaneously using free-fall-type and box-type apparatuses in the same seabed area. However, there is a problem in that samples are disturbed in the process in which the sample box digs into the sediment. Further, since the sample box of the collection apparatus is integrally configured in the collection apparatus, there is a problem in that, after moving the collection apparatus onto the deck of the ship, it is impossible to transport the sample accommodated in the sample box of the collection apparatus to a laboratory without disturbing the sample.

SUMMARY OF THE INVENTION

The present disclosure provides a mechanism for stably collecting sediment from the seabed without disturbing the same by operating a sample collection apparatus with a simple operation.

The present disclosure also provides a mechanism for enabling a sample collection box, which contains a collected sample, to be separated from a sample collection apparatus such that the sample collection box can be easily transported to a laboratory or the like.

Further, the technical problems of the present disclosure are not limited to those described above, and other technical subjects, which are not described above, will be clearly understood by a person ordinarily skilled in the art to which the present disclosure belongs, from the following description.

The above-described aspects are achieved by a sample collection apparatus according to the present disclosure, which includes: a frame section having a lower frame seated on a seabed surface and an opening provided in a horizontal direction at one side thereof, an upper frame connected to the lower frame and having an operation hole formed in a center thereof, and an operation space formed between the upper and lower frames; a vertical operation section including: a vertical operation member provided through the operation hole to be vertically movable, and including weights provided on left and right sides of a lower portion thereof, and a trigger device provided at an upper end thereof, to be connected to a lifting cable; and a box-mounting unit provided at a lower end of the vertical operation member located in the operation space, and configured such that a sample collection box having opened upper and lower portions is mounted thereon or detached therefrom; and a rotary operation section having a pair of rotary members coupled to both side surfaces of the box-mounting unit by rotary shafts, wherein one ends of the rotary members are connected to the trigger device by pulling cables and an arc-shaped box opening/closing member is provided at the other ends of the rotary members, and the rotary operation section is configured such that, after the frame section is seated on the seabed, the trigger device is operated, and the vertical operation member descends such that the sample collection box mounted on the box-mounting unit digs into the seabed surface, the rotary members are rotated about the rotary shafts by pulling of the pulling cable such that the box opening/closing member closes the opened lower portion of the sample collection box so as to prevent the sample from flowing out.

The trigger device may include: a lifting connector, of which an upper end is connected to the lifting cable, both ends connected to the pulling cables, respectively, and a lower end is formed with an engagement hole; a hook member, of which one end is coupled to the inside of the upper end of the vertical operation member by a support shaft and the other end is formed with a hook configured to be hooked into the engagement hole; and a rotation prevention hook member, of which one end is coupled to the support shaft to be rotationally operated together with the hook member within a predetermined angle such that, when the rotary members are rotated upward about the rotary shafts by the pulling operation of the pulling cables, the rotation prevention hook member is engaged with an engagement step provided at one end of the rotary member so as to prevent the rotation of the rotary member. The hook member may be formed at a position shifted to one side such that a vertical center line of the hook is deviated from a vertical center line of the support shaft such that, when the frame section is seated on the seabed surface and the lifting connector, from which tension is removed, descends so that the hook is disengaged from the engagement hole, the hook member may be rotated to a direction shifted to one side about the support shaft to be separated from the lifting connector.

The trigger device may further include a safety pin passing through an upper end portion of the vertical operation member and the hook, and a pair of guide rollers, which are respectively provided on both side surfaces of upper end portion of the vertical operation member so as to support and guide the pulling cable.

The box-mounting unit may be provided with an outflow prevention mechanism configured to prevent the sample from flowing out by covering the opened upper portion of the sample collection box in response to the release operation of the trigger device when the frame section is seated on the seabed and the sample collection box digs into the seabed surface. The outflow prevention mechanism may include: an upper cover, of which one end is coupled to one side of the bottom surface of the box-mounting unit by a hinge so as to rotate around the hinge to cover the upper portion of the sample collection box; and an opening/closing wire, of which one end is coupled to the upper cover and the other end is connected to a region shifted to one side in a hook member. The opening/closing wire may be configured such that, when the hook member is coupled to the lifting connector, the opening/closing wire lifts up the upper cover so as to open the sample collection box and when the hook member is separated from the lifting connector and is rotated toward the region shifted to one side, the opening/closing wire is relaxed so as to cause the upper cover to rotate by the self-weight thereof and to cover the upper portion of the sample collection box.

In the upper end portion of the vertical operation member, a pair of arc-shaped guide holes may be formed to face each other, and in the guide holes, a guide pin, to which the other end of the opening/closing wire is connected, may be installed through the region shifted to one side in the hook member.

The box-mounting unit may include a horizontal guide mechanism such that the sample collection box moving in a horizontal direction through the opening is slid to be coupled thereto or detached therefrom, and the horizontal guide mechanism may include guide rails provided on both sides of the inside of the box-mounting unit to face each other, and guide stages, which are respectively provided on the both side surfaces of the sample collection box, which face the guide rails, to be slidably engaged with the guide rails.

The box-mounting unit is provided with a mounting mechanism configured to fix or release a position of the sample collection box which has entered the inside of the box-mounting unit by the horizontal guide mechanism, and the mounting mechanism may include a pair of support brackets respectively having arc-shaped operation holes on both sides of the inside of the box-mounting unit and coupled to face each other; an operation bracket, of which one end is formed with an engagement hook opened downward, a middle portion is coupled to the support brackets by a shaft to be rotated by a predetermined angle, and the other end is formed with a handle; a position-fixing shaft installed through the middle region of the operation bracket, which corresponds to the arc-shaped operation holes, the both ends of the position-fixing shaft being exposed through the arc-shaped holes, and a tightening nut being selectively fastened to each of opposite ends of the position-fixing shaft so as to fix the position of the operation bracket. When the sample collection box is made to enter the inside of the box-mounting unit by the horizontal guide mechanism, the operation bracket may be rotated such that the engagement hook is engaged with the mounting engagement bar provided on one surface of the sample collection box, and then the tightening nuts may be tightened such that the position of the operation bracket is fixed and the sample collection box is mounted on the box-mounting unit.

The sample collection box may further include a collection box cover member, which is configured such that, in a state in which the box opening/closing member closes the lower portion of the sample collection box, the collection box cover member is inserted between the box opening/closing member and the digging portion of the sample collection box to be coupled to the sample collection box while closing the opened lower end of the sample collection box so as to prevent collected sample from flowing out.

In a lower region of the vertical operation member, a descent prevention mechanism is provided in order to prevent a descending operation of the vertical operation member in a state in which the frame section is seated on the ground or on the deck of a ship. The descent prevention mechanism may include a stop hole formed through the vertical operation member and a stop pin installed through the stop hole in order to prevent descent of the vertical operation member.

The sample collection apparatus may further include a moving carriage configured to horizontally move the sample collection box toward the inside of the box-mounting unit in the state in which the frame section is seated on the ground or on the deck of a ship in order to mount the sample collection box on the box-mounting unit, or to move the sample collection box detached from the box-mounting unit.

The moving carriage may include a seat portion configured to seat the sample collection box on an upper surface thereof and a play prevention rope configured to fix the sample collection box so as to prevent the sample collection box seated on the seat portion from moving freely while being transported.

According to the present disclosure, it is possible to stably collect sediment from the seabed without disturbing the same by operating the sample collection apparatus by a simple operation. Since the operation structure at the time of installation of the sample collection apparatus is simple, it is possible to stably perform operation thereof on a ship. In addition, it is possible to provide an effect in which the collected sample can be stably transported using a moving carriage.

Further, since the sample collection box is configured to be movable in the horizontal direction to be mounted on the box-mounting unit or to be moved in the horizontal direction after being detached, it is possible to easily mount, detach, and transport the sample collection box.

BRIEF DESCRIPTION OF THE DRAWINGS

The above and other aspects, features and advantages of the present disclosure will be more apparent from the following detailed description taken in conjunction with the accompanying drawings, in which.

DETAILED DESCRIPTION OF THE EXEMPLARY EMBODIMENTS

Hereinafter, exemplary embodiments of the present disclosure will be described in detail with reference to the accompanying drawings. In the description of the present disclosure, the description of the well-known function or structure will be omitted in order to clear the subject matter of the present disclosure.

Figure 1:
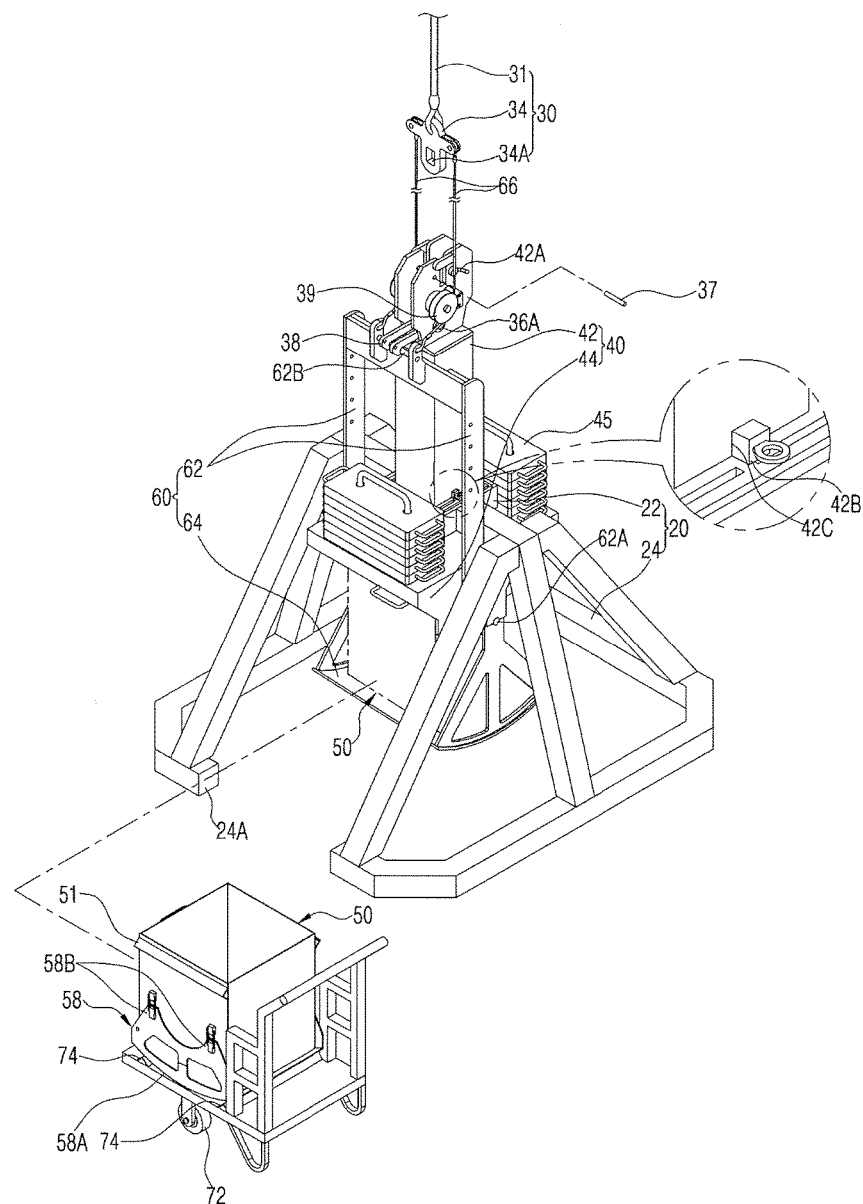
FIG. 1 is an exploded perspective view illustrating a sample collection apparatus according to the present disclosure.
Figure 2:
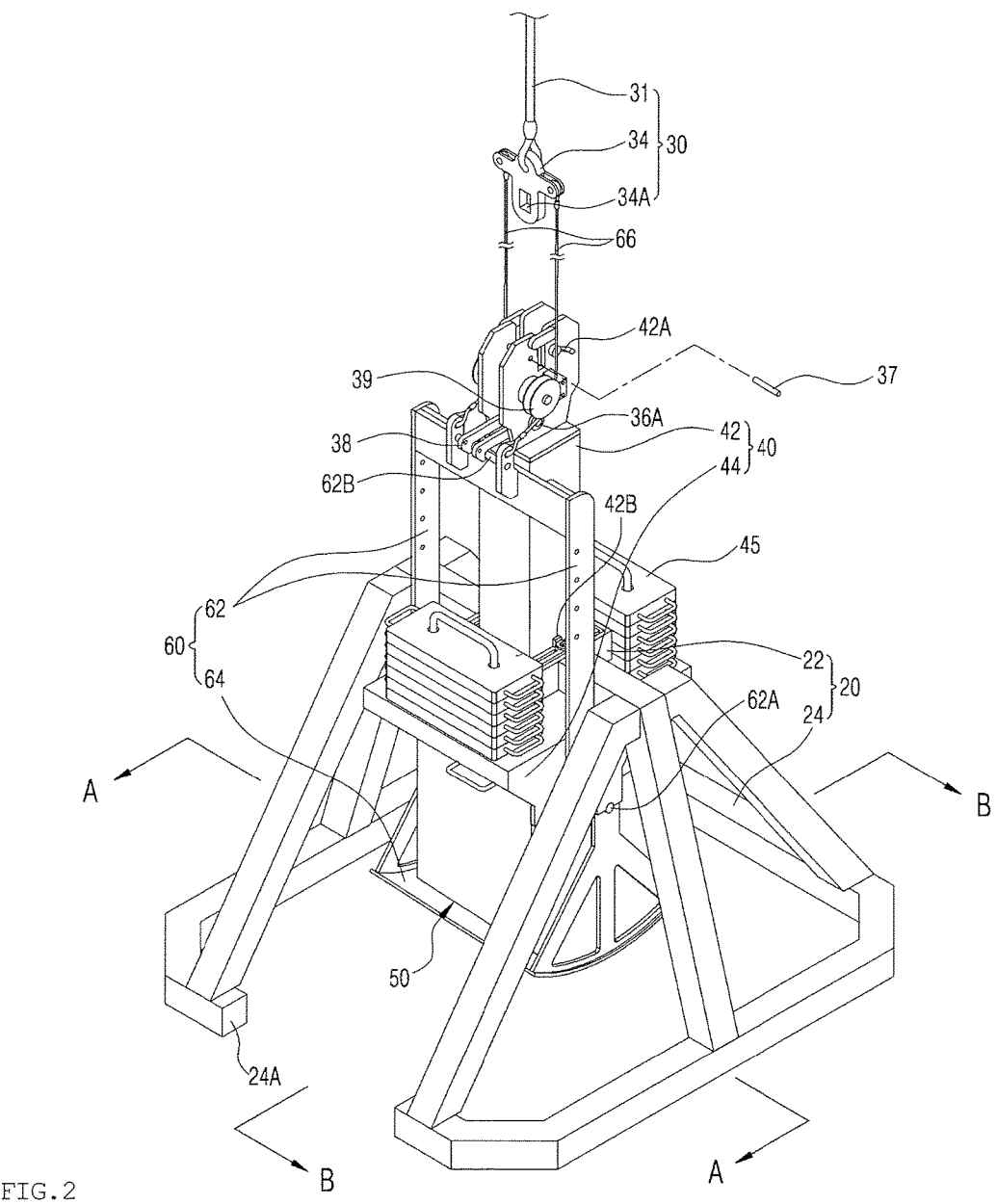
FIG. 2 is a perspective view illustrating the coupled state of the sample collection apparatus illustrated in FIG. 1.
Figure 3:
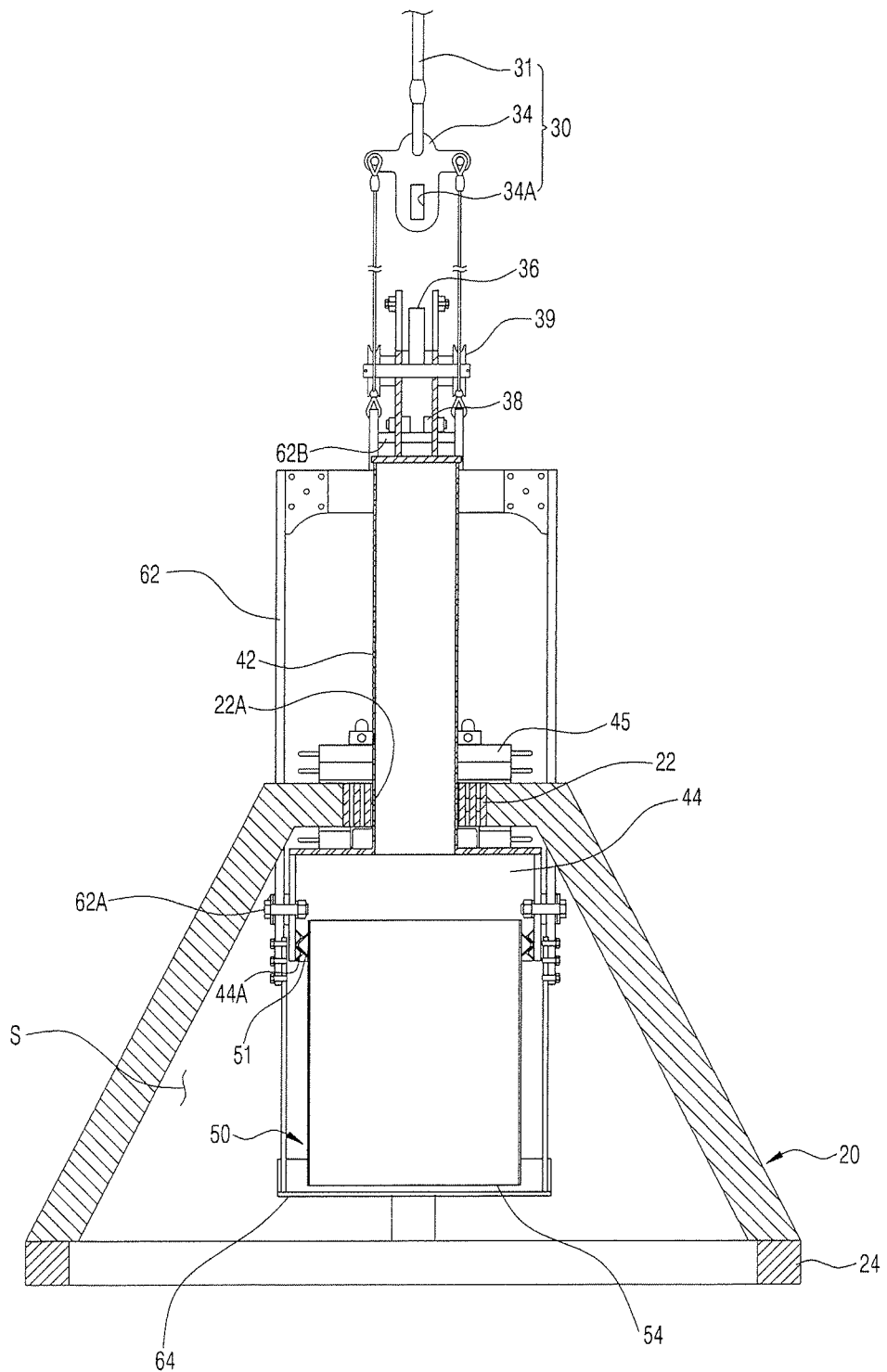
FIG. 3 is a schematic cross-sectional view taken along line A-A in FIG. 2.
Figure 4:
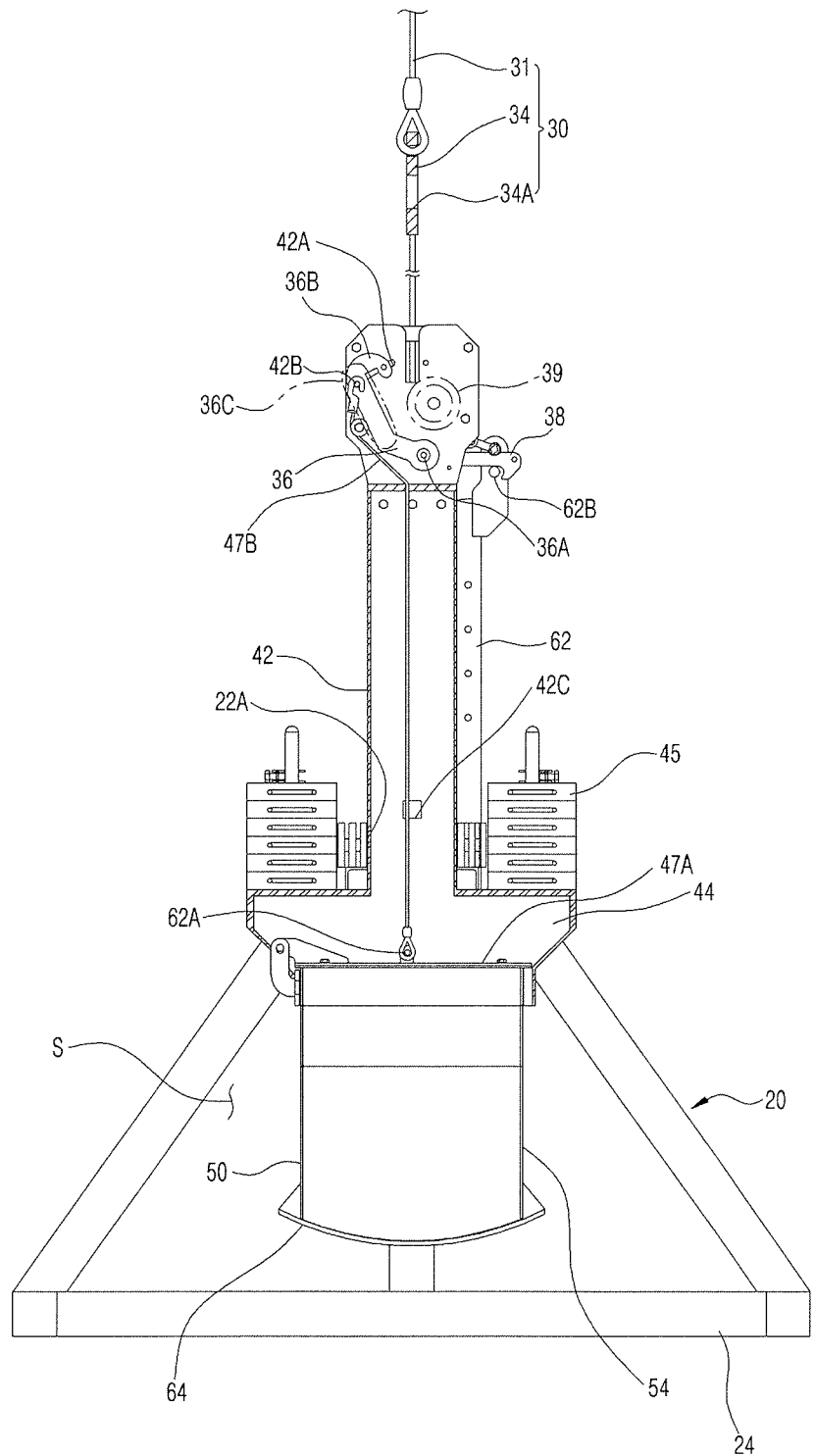
FIG. 4 is a schematic cross-sectional view taken along line B-B in FIG. 2.

In the accompanying drawings, FIG. 1 is an exploded perspective view illustrating a sample collection apparatus according to the present disclosure, FIG. 2 is a perspective view illustrating the coupled state of the sample collection apparatus illustrated in FIG. 1, and FIG. 3 is a schematic cross-sectional view taken along line A-A in FIG. 2. In addition, FIG. 4 is a schematic cross-sectional view taken along line B-B in FIG. 2.

As illustrated in FIGS. 1 to 4, a sample collection apparatus according to the present disclosure includes a frame section 20 having a quadrangular pyramid shape; a vertical operation section 40, an upper end of which is connected to a lifting cable 31 and is provided with a trigger device 30 so as to be coupled to the frame section 20 to be vertically movable and a lower end of which is provided with a box-mounting unit 44, which is downwardly opened; and a rotary operation section 60 configured to rotationally operate when the frame section 20 is seated on the seabed and the lower end of a sample collection box 50 digs into the seabed surface so as to prevent the loss of a collected sediment sample by closing the lower portion of the sample collection box 50.

The sample collection apparatus will be described in more detail below.

As illustrated in FIGS. 1 and 2, the frame section 20 has a quadrangular pyramid shape overall. The frame section 20 includes: a lower frame 24 formed to be stably seated on the seabed surface, and having a rectangular opening 24A formed in a horizontal direction at one side thereof; and an upper frame 22 configured with respective columns, which are coupled to the upper surface of the lower frame 24 so as to be inclined upwardly, and having an operation hole 22A formed in a vertical direction at the upper end thereof. Due to the structures of the lower frame 24 and the upper frame 22 described above, an operation space S is formed inside the frame section 20, and by having the quadrangular pyramid shape overall, the frame section 20 can be stably mounted on the seabed surface.

A vertical operation section 40 is provided over the operation hole 22A of the frame section 20 so as to be movable up and down so that, when a trigger device 30 is released, the vertical operation section 40 descends due to the weight of weights 45 so as to cause a sample collection box 50 mounted on a box-mounting unit 44 to dig into the sediment layer on the seabed surface. In the vertical operation section 40, the vertical operation member 42 is installed on the operation hole 22A so as to be movable up and down through the operation hole 22A, the weights 45 are installed on the lower left and right sides of the vertical operation member 42, respectively, and the trigger device 30 is provided on the upper end of the vertical operation section 40 to be connected to a lifting cable 31. The box-mounting unit 44 having an opened lower portion is coupled to the lower end of the vertical operation member 42 located in the operation space S, the box-mounting unit 44 being configured such that the sample collection box 50 having opened upper and lower portions is mounted thereon or detached therefrom.

As illustrated in FIGS. 1, 2 and 4, the vertical operation member 42 has a rectangular tube shape, and the upper end of the vertical operation member 42 has a structure in which two plate members, each having a predetermined length and width, are coupled to face each other. The trigger device 30 is coupled to the upper end of the vertical operation member 42.

As illustrated in FIGS. 1 and 2, the weights 45 are fixed to the top surfaces of the left and right sides of the box-mounting unit 44 coupled to the lower region of the vertical operation member 42.

In addition, in the upper end portion of the vertical operation member 42, a pair of arc-shaped guide holes 42A is formed in a direction, in which a hook member 36 of the trigger device 30 rotates about a support shaft 36A, to face each other. In addition, in the guide holes 42A, a guide pin 42B, to which the other end of an opening/closing wire 47B is connected, is installed through a region 36C shifted to one side in the hook member 36.

This structure is provided in order to ensure that, when the hook member 36 released by the operation of the trigger device 30 rotates the region 36C shifted to one side, the guide pin 42B, to which the other end of the opening/closing wire 47B is connected, moves along the arc-shaped guide hole 42A, whereby the tensioned state of the opening/closing wire 47B, which has been tensioned by pulling upward an upper cover 47A is released, so that the upper cover 47A covers the upper portion of the sample collection box 50.

In the lower region of the vertical operation member 42, a descent prevention mechanism is provided in order to prevent the descending operation of the vertical operation member 42 in the state in which the frame section 20 is seated on the ground or on the deck of a ship. The descent prevention mechanism includes a stop hole 42C formed through the vertical operation member 42 and a stop pin 42B installed through the stop hole 42C to be engaged with the operation hole 22A, thereby preventing the descent of the vertical operation member 42. The descent prevention mechanism prevents the vertical operation member 42 from being moved accidentally by inserting the stop pin 42B into the stop hole 42C when the sample collection apparatus is placed on the ground or on the deck of a ship.

The box-mounting unit 44 is coupled to the lower end of the vertical operation member 42, in which the box-mounting unit 44 is configured to mount the sample collection box 50 thereon or to detach the sample collection box 50 therefrom, and the upper and lower portions of the sample collection box 50 are opened.

The box-mounting unit 44 has a structure, the lower portion of which is opened, and includes a horizontal guide mechanism such that the sample collection box 50 moving in a horizontal direction through the opening 24A in the frame section 20 is slid to be coupled thereto or detached therefrom. The opening 24A described above is formed at one side of the lower frame 24 (in the direction in which the sample collection box moves horizontally) so as to allow a moving carriage 70 to enter the working space S formed inside the frame section 20, so that the moving carriage 70 can be smoothly moved through the opening 24A.

The horizontal guide mechanism includes guide rails 44A provided on both sides of the inside of the box-mounting unit 44 to face each other, and guide stages 51, which are respectively provided on the both side surfaces of the sample collection box 50, which face the guide rails 44A, to be slidably engaged with the guide rails 44A. The sample collection box 50 can be horizontally moved by the horizontal guide mechanism to be mounted on or detached from the box mounting portion 44. At this time, although not illustrated in the drawings, moving rollers may be installed on the guide rails 44A or the guide stages 51.

Figure 10:
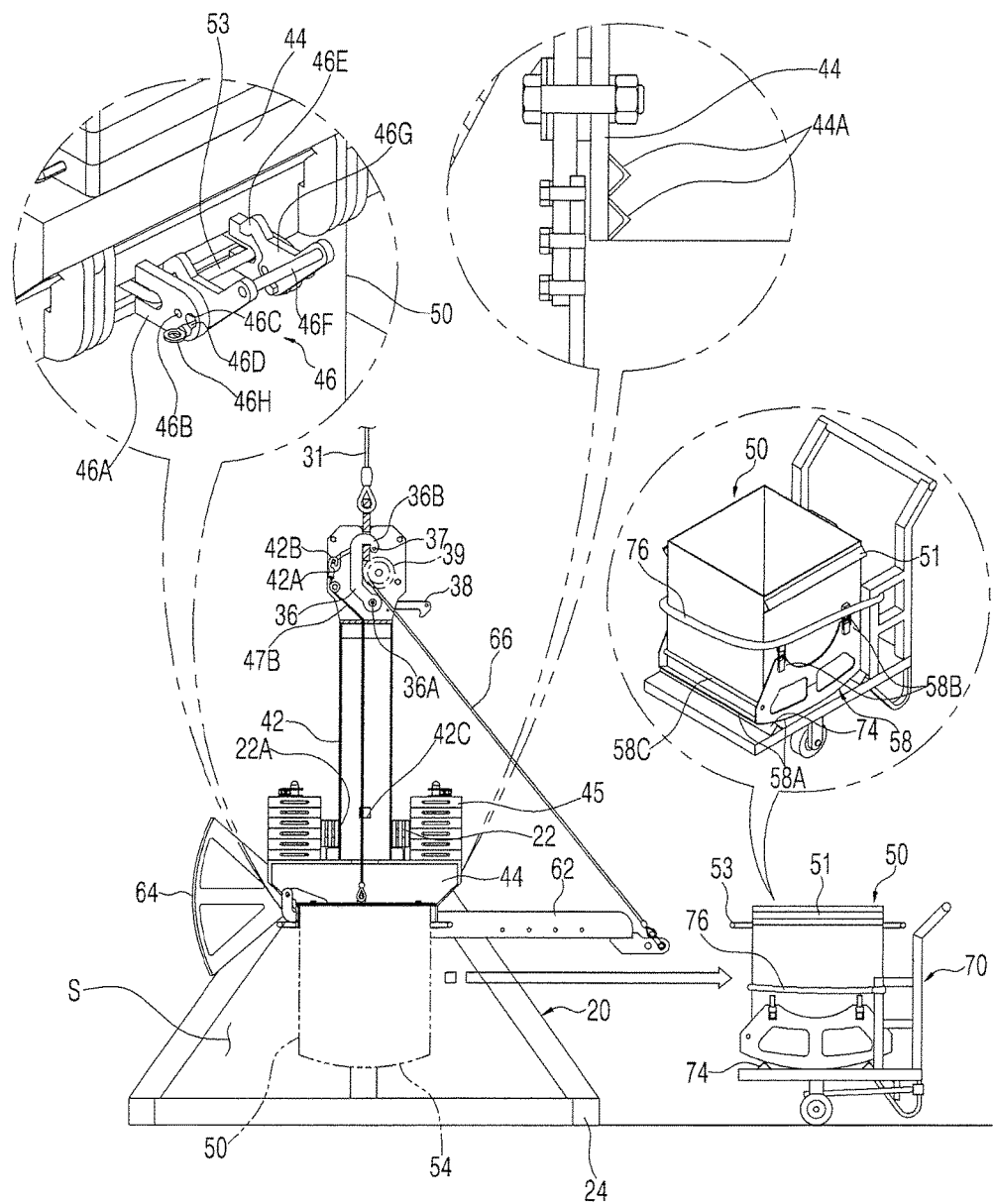
FIG. 10 is a view illustrating a state in which the sample collection box is detached from a box-mounting unit and carried by a moving carriage.

Meanwhile, the box-mounting unit 44 is provided with a mounting mechanism 46 configured to fix or release the position of the sample collection box 50 which has entered the inside of the box-mounting unit 44 by the horizontal guide mechanism. As illustrated in FIG. 10, a mounting mechanism 46 includes: a pair of support brackets 46A respectively having arc-shaped operation holes 46C both sides of the inside of the box-mounting unit 44 and coupled to face each other; an operation bracket 46G, of which one end is formed with an engagement hook 46E opened downward, a middle portion is coupled to the support brackets 46A by a shaft 46B to be rotated by a predetermined angle, and the other end is formed with a handle 46F; a position-fixing shaft 46D installed through middle region of the operation bracket 46G, which corresponds to the arc-shaped operation holes 46C, the both ends of the position-fixing shaft 46D being exposed through the arc-shaped holes 46C, and a tightening nut 46H being selectively fastened to each of the opposite ends of the position-fixing shaft 46D so as to fix the positions of the operation bracket 46G.

When the sample collection box 50 enters the inside of the box-mounting unit 44 by the horizontal guide mechanism, the mounting mechanism 46 rotates the operation bracket 46G toward an engagement bar 53 formed on the sample collection box 50 so that both engagement hooks 46E are engaged with the mounting engagement bar 53 provided on one surface of the sample collection box 50, and then each of the tightening nuts 46H provided on the both ends of the position-fixing shaft 46D is tightened such that the operation bracket 46G is not rotated accidentally.

When the operation brackets 46G are rotated and fixed in this manner, the sample collection box 50 can be easily mounted on or detached from the box-mounting unit 44.

On the other hand, the box-mounting unit 44 is provided with an outflow prevention mechanism configured to prevent the sample from flowing out by covering the opened upper portion of the sample collection box 50 in response to the release operation of the trigger device 30 when the frame section 20 is seated on the seabed and the sample collection box 50 digs into the seabed surface.

Figure 5:
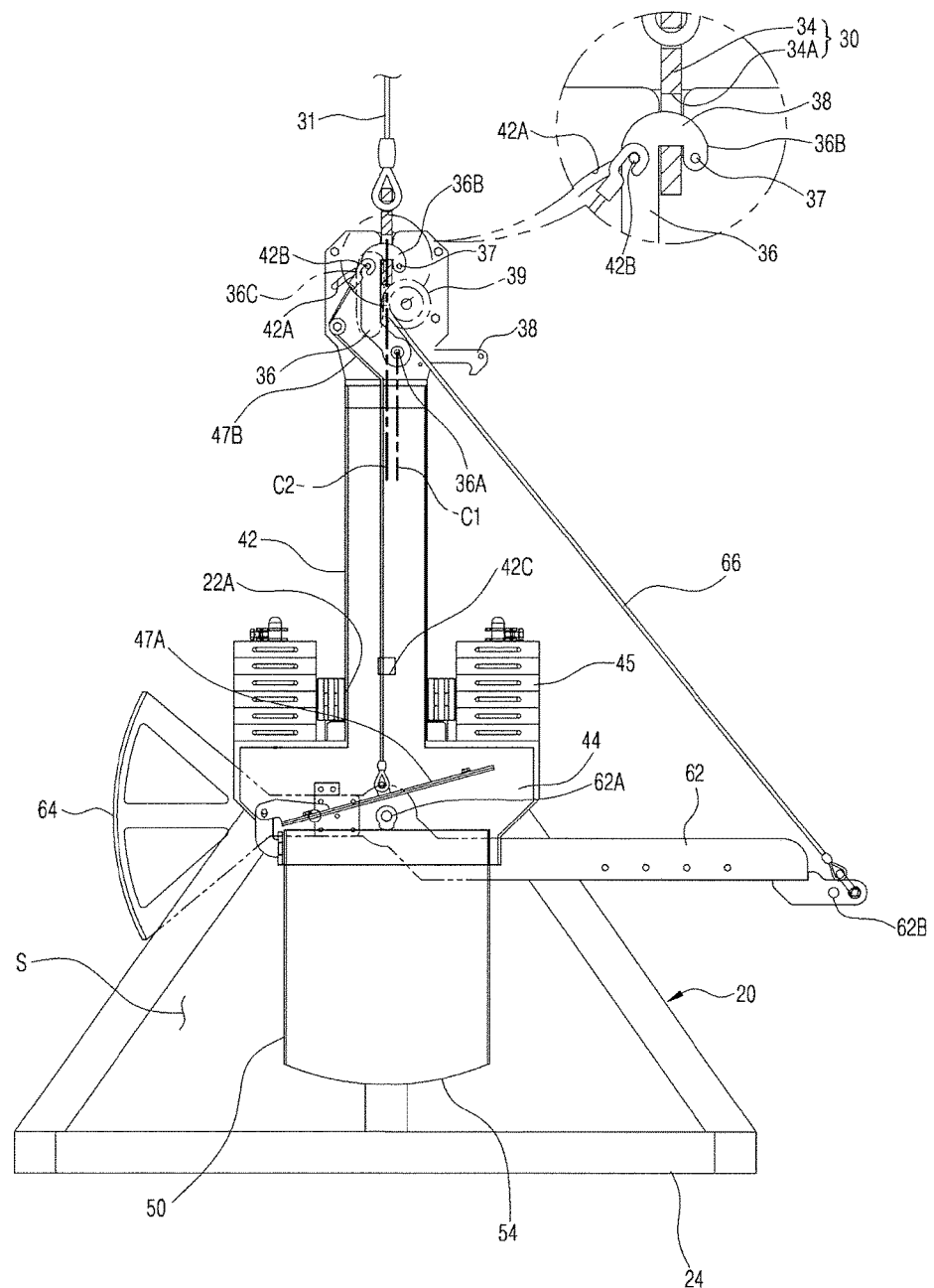
FIGS. 5 to 8 are views illustrating operational states for describing a procedure of collecting sediment from the seabed using the sample collection apparatus illustrated in FIG. 1.

As illustrated in FIG. 4 or FIG. 5, the outflow prevention mechanism includes: an upper cover 47A, of which one end is coupled to one side of the bottom surface of the box-mounting unit 44 by a hinge so as to rotate around the hinge to cover the upper portion of the sample collection box 50, and an opening/closing wire 47B, of which one end is coupled to the upper cover 47A

A and the other end is connected to a region 36C shifted to one side in a hook member 36, which constitutes the trigger device 30. The opening/closing wire 47B is configured such that, when the hook member 36 is coupled to the lifting connector 34, the opening/closing wire 47B lifts up the upper cover 47A so as to open the sample collection box 50 and when the hook member 36 is separated from the lifting connector 34 and is rotated toward the region shifted to one side, the opening/closing wire 47B is relaxed so as to cause the upper cover 47A to rotate by the self-weight thereof and to cover the upper portion of the sample collection box 50.

Such an outflow prevention mechanism is capable of preventing the sample from flowing out through the opened upper portion of the sample collection box 50.

The trigger device 30 is adapted to perform a release operation so that when the frame section 20 is seated on the seabed surface, the rotary operation section 60 starts a rotation operation. The trigger device 30 includes: the lifting connector 34, of which the upper end is connected to the lifting cable 31, both ends are respectively connected to pulling cables 66, each coupled to one end of each rotary member 62, and the lower end is formed with a vertically elongated engagement hole 34A; the hook member 36, of which one end is coupled to an upper inner side of the vertical operation member 42 by a support shaft 36A and the other end is formed with a hook 36B configured to be engaged with the engagement hole 34A; and a rotation prevention hook member 38, of which one end is coupled to the support shaft 36A to be rotationally operated together with the hook member 36 within a predetermined angle such that, when the rotary member 62 is rotated upward about the rotary shaft 62A by the pulling operation of the pulling cables 66, the rotation prevention hook member 38 is engaged with an engagement step 62B provided at one end of the rotary member 62 so as to prevent the rotation of the rotary member 62.

As illustrated in FIG. 5, the vertical center line C2 of the hook 36B is located at a position deviated from the vertical center line C1 of the support shaft 36A. That is, the hook 36B is formed to be biased to one side about the support shaft 36A. Such a hook member 36 is configured such that, when the frame section 20 is seated on the seabed surface and the pulling force acting on the lifting connector 34 is removed so that the hook 36B of the lifting connector 34 is released from the engagement hole 34A, the hook member 36 is rotated toward the region 36C shifted to one side about the support shaft 36A and is separated from the lifting connector 34.

That is, the hook member 36 extends upward from the lower end thereof, which is coupled to the support shaft 36A, to be shifted to one side, and then the hook 36B is formed at an upper end of the hook member 36, so that, in the vertically erect state, the hook member 36 is rotated toward the region 36C shifted to one side by the self-weight thereof. Therefore, when the pulling force of the lifting cable 31 is relaxed in the state in which the hook 36B is engaged with the lifting connector 34 so that the lifting connector 34 descends, the hook member 36 is rotated about the support shaft 36A, so that the hook 36B can be disengaged from the engagement hole 34A, and as a result, the engagement between the lifting connector 34 and the hook member 36 is released.

Meanwhile, the trigger device 30 further includes a safety pin 37 passing through the hook 36B and the upper end of the vertical operation member 42, and a pair of guide rollers 39 installed at the opposite sides of the upper end of the vertical operation member 42 so as to support and guide the pulling cable 66.

The safety pin 37 is provided to penetrate the upper end portion of the vertical operation member 42 and the hook member 36 such that the hook member 36 is not accidentally disengaged. That is, when the sample collection device is located on the ground or on the deck of a ship, the hook member 36 is coupled to the vertical operation member 42 so as to prevent the trigger device 30 from operating, and the disengagement operation of the trigger device 30 can be performed only when the safety pin 37 preventing the operation of the hook member 36 is removed.

The rotation prevention hook member 38 is coupled to the support shaft 36A at one end thereof. When the rotary member 62 is rotated toward the trigger device 30, the engagement step 62B is engaged with the end in order to maintain the rotation completion state of the rotary member 62 (a state in which the box opening/closing member closes the lower portion of the sample collection box). The rotation prevention hook member 38 is provided with a spring so as to always be in a fixed position, and is configured to be interlocked with the hook member 36. That is, when the hook member 36 is released from the engagement to be rotated toward the guide hole 42A, the rotation prevention hook member 38 is also rotated upward, thereby releasing the engagement of the engagement step 62B.

When the frame section 20 is seated on the seabed and the trigger device 30 is operated, the rotary operation section 60 is rotated upward about the rotary shaft 62A by the pulling cable 66 connected to the lifting cable 31 so as to cover the lower portion of the sample collection box 50, which digs into sediment in order to prevent the collected sample from flowing out. A pair of rotary members 62 is provided on the both sides of the box-mounting unit 44 via the rotary shaft 62A, and the one ends of the rotary members 62 are connected to the lifting connector 34 of the trigger device 30 by the pulling cables 66 and the other ends of the rotary members 62 are provided with an arc-shaped box opening/closing member 64.

As illustrated in FIG. 1, the box opening/closing member 64 is formed in an arc shape having the same curvature as the lower end of the sample collection box 50. This is to enable the rotary member 62 to close the arc-shaped and opened lower end portion of the sample collection box 50 without interfering with the lower end portion of the arc-shaped sample collection box 50 when the rotary member 62 rotates about the rotary shaft 62A.

In addition, the rotary member 62 has a structure bent to a position that is deviated from the vertical center line of the rotary shaft 62A from the region in which the rotary member 62 is coupled to the rotary shaft 62A to the region in which the engagement step 62B is provided. This is to enable the engaging step 62B to be easily engaged with the rotation prevention hook member 38, which protrudes to one side.

The sample collection box 50 has a rectangular box shape having opened upper and lower portions, and an arc-shaped digging portion 54 having the same curvature as the curvature of the box opening/closing member 64 is formed in the lower end of the sample collection box 50. The arc-shaped digging portion 54 facilitates engagement with the box opening/closing member 64, facilitates digging into the seabed surface sediment layer, and facilitates engagement with the sampling box cover member 56.

An engagement bar 53 protrudes from an upper region of one side of the sample collection box 50. The engagement bar 53 is configured to be engaged with the engagement hook 46E of the operation bracket 46G.

The sample collection box 50 further includes a collection box cover member 58, which is configured such that, in the state in which the box opening/closing member 64 closes the lower portion of the sample collection box 50 so as to prevent the collected sample from flowing out, the collection box cover member 58 is inserted between the box opening/closing member 64 and the digging portion 54 of the sample collection box 50 to be coupled to the sample collection box 50 while closing the opened lower end of the sample collection box 50 so as to prevent the sample collected in the sample collection box 50 from flowing out while the sample collection box 50 is being transported.

As illustrated in FIG. 10, the sample collection box cover member 58 has a structure in which a blocking portion 58A is formed in the shape of an arc-shaped plate, which has the same curvature as the digging portion 54 in the sample collection box 50, in the lower end of the sample collection box 50, the blocking portion 58A is bent upward at the opposite sides thereof to form coupling portions 58B, respectively, and each of the coupling portions 58B is provided with a so-called cicada loop clamp at an end thereof.

In addition, a movement restriction bar 58C is provided on one side of the collection box cover member 58 in order to prevent the collection box cover member 58 from being released from the sample collection box 50 when the collection box cover member 58 is inserted between the box opening/closing member 64 and the digging portion 54 of the sample collection box 50.

Therefore, in the state in which the collection box cover member 58 is inserted between the box opening/closing member 64 and the digging portion 54 of the sample collection box 50, the loops of the cicada loop clamps are engaged with the loops provided on the both side surfaces of the sample collection box 50, so that the collection box cover member 58 can be coupled to be integrated with the sample collection box 50.

Meanwhile, the sample collection apparatus according to the present disclosure further includes a moving carriage 70 configured to horizontally move the sample collection box 50 toward the inside of the box-mounting unit 44 in the state in which the frame section 20 is seated on the ground or on the deck of a ship in order to mount the sample collection box 50 on the box-mounting unit 44, or to move the sample collection box 50 detached from the box-mounting unit 44.

The moving carriage 70 includes a moving wheel 72 and a handle, and is provided with a seat portion 74 configured to seat the sample collection box 50 on the upper surface thereof and a play prevention rope 76 configured to fix the sample collection box 50 so as to prevent the sample collection box 50 seated on the seat portion 74 from freely moving while being transported. The seat portion 74 is constituted with two bars installed to be spaced apart from each other such that the bottom surface of the arc-shaped bottom surface of the collection box cover member 58 is seated thereon, and the play prevention rope 76 is fixed to a support that is vertically erect on one side of the moving carriage 70. At this time, the end of the play prevention rope 76 may be provided with a cicada loop clamp.

Hereinafter, a process of collecting a sediment sample from the seabed surface using the sample collection apparatus constructed as described above will be described.

First, as illustrated in FIG. 5, the lifting cable 31 connected to the crane is connected to the lifting connector 34 and the hook 36B of the hook member 36 is connected to the engagement hole 34A in the lifting connector 34. Of course, since the safety pin 37 is removed and the lifting cable 31 is pulled by the crane, the lifting connector 34 and the hook member 36 are kept in a tensioned state. In addition, the rotary operation section 60 is rotated horizontally.

Figure 6:
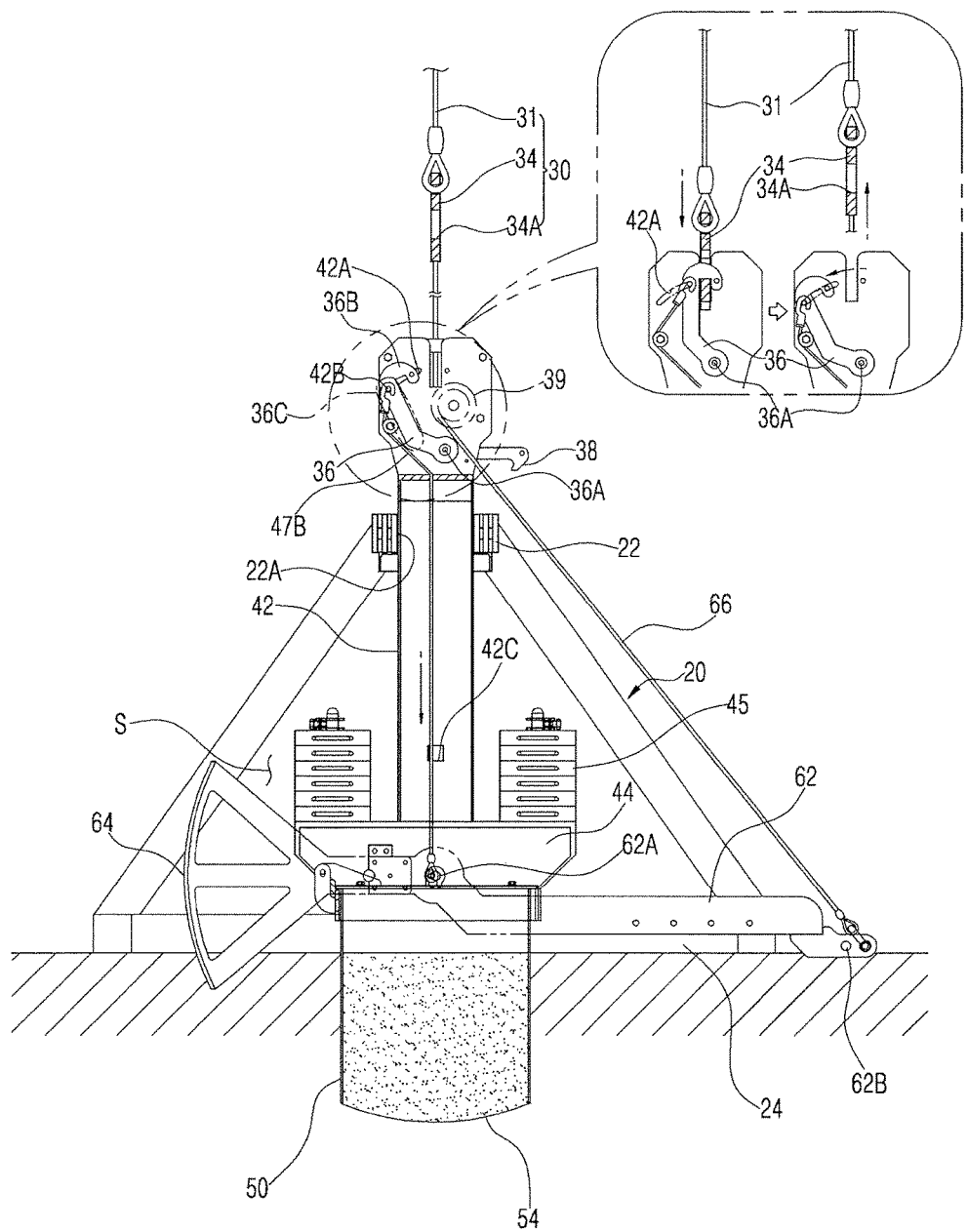

In this state, as illustrated in FIG. 6, when the sample collection apparatus is seated on the seabed surface by the crane, the vertical operation member 40 is moved downward through the operation hole 22A by the weight of the weights 45, and during this process, the digging portion 54 in the sample collection box 50 mounted on the box-mounting unit 44 digs into the sediment layer of the seabed.

Meanwhile, as illustrated in FIG. 6, since the lifting connector 34 descends simultaneously when the lower frame 24 is seated on the seabed surface, the tensioned state of the lifting connector 34 and the hook member 36 is released, and as a result, the hook member 36 is rotated to the direction in which the guide hole 42A is formed, so that the hook 36B is detached from the engagement hole 34A and the engagement is thus released. At this time, the descending distance of the lifting connector 34 is set to an extent such that the hook member 36 is detached, and when the hook member 36 is detached, the lifting connector 34 is placed in the state in which it can be raised.

Since the guide pin 42B is guided by the guide hole 42A to move downward as the hook member 36 is rotated to a direction shifted to one side as described above, the opening/closing wire 47B, which pulls the upper cover 47A upward, is lowered so that the upper cover 47A covers the upper portion of the sample collection box 50, thereby preventing the collected sample from flowing out.

Figure 7:
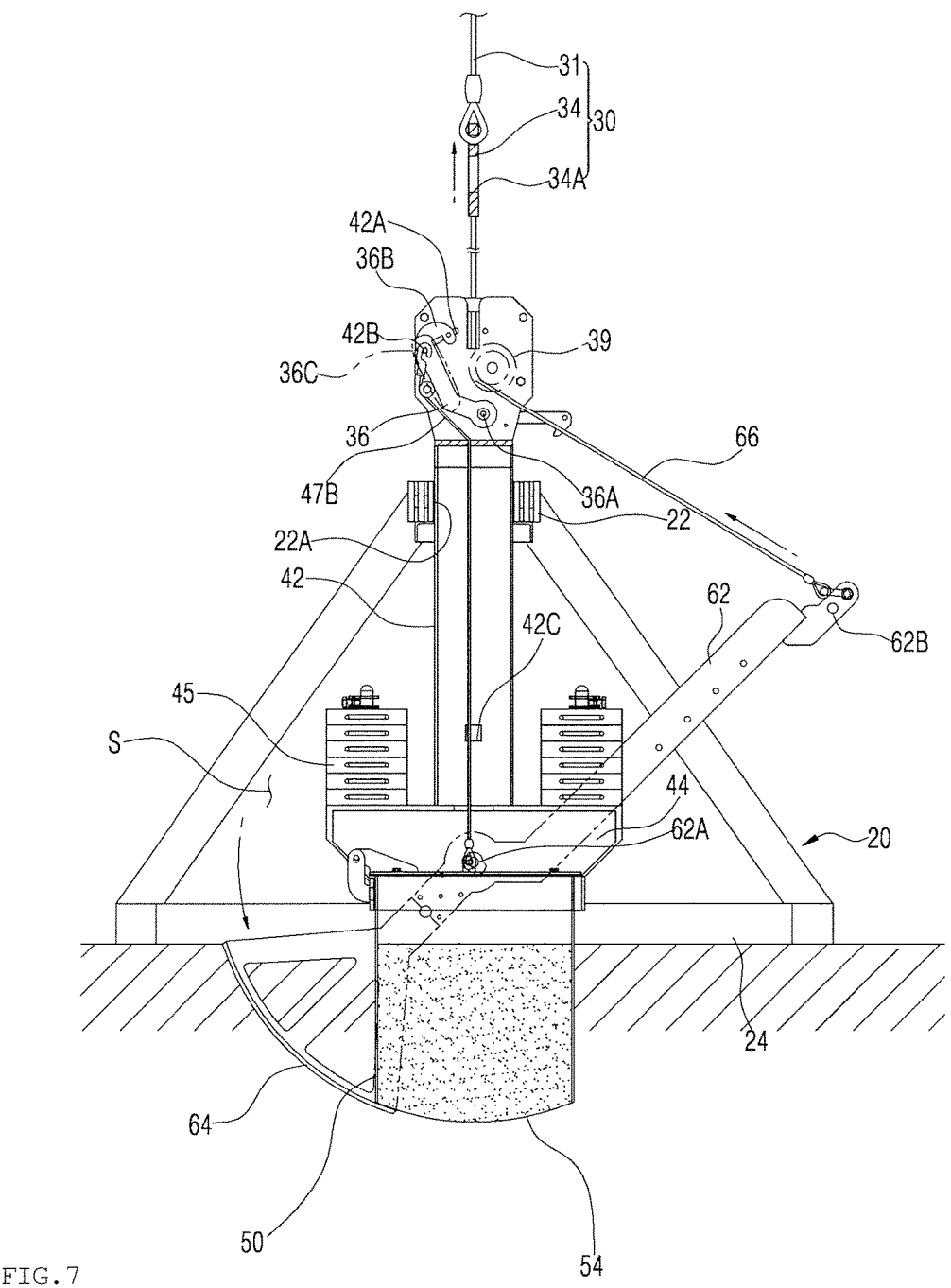
Figure 8:
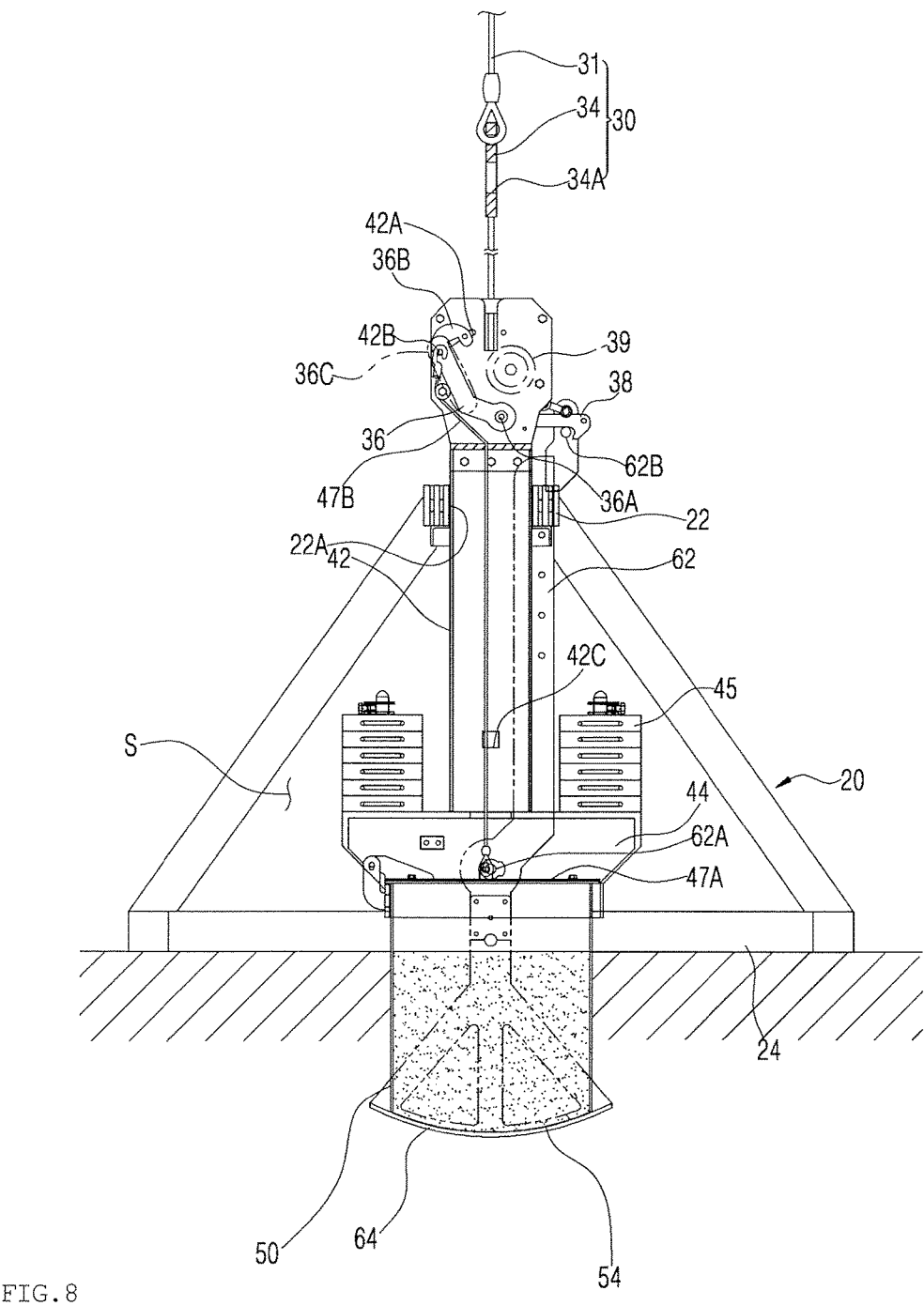

Subsequently, as illustrated in FIG. 7, when the crane is operated and the lifting connector 34 ascends, the pulling cable 66 is pulled upward so as to rotate the rotary operation section 60 placed in a horizontal state. When the rotary operation section 60 is rotated, as illustrated in FIG. 8, the box opening/closing member 64 is rotated to the lower side of the sample collection box 50 to block the lower portion of the sample collection box 50, thereby preventing the sample from flowing out. At the same time, the engagement step 62B of the rotary member 62 is engaged with the rotation prevention hook member 38 so that the upwardly rotated state of the rotary member 62 is fixed.

Figure 9:
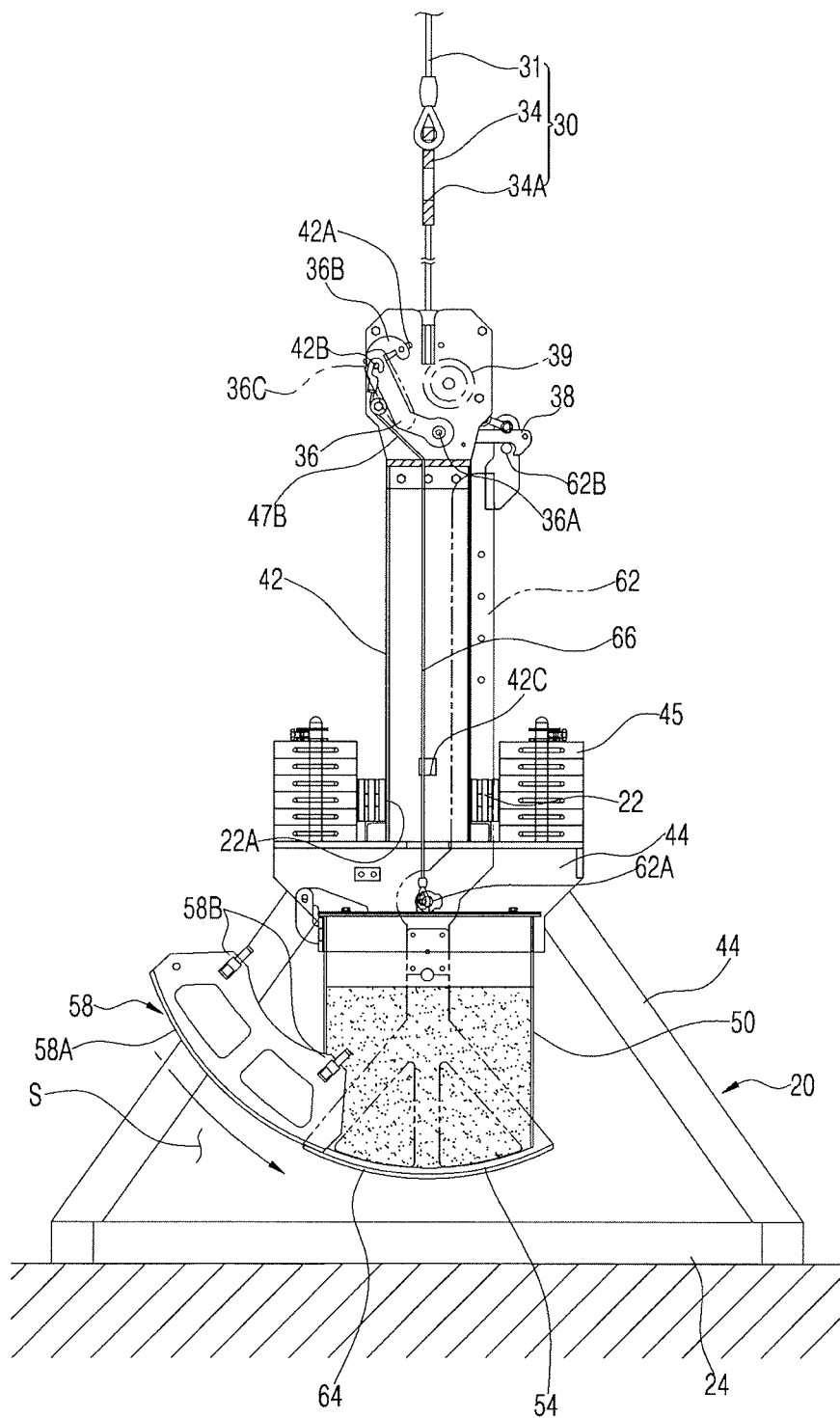
FIG. 9 is a view illustrating a state in which a collection box cover member is mounted on a sample collection box.

When the sample collection box is lifted up from the deck of a ship through the above-described process, as illustrated in FIG. 9, the collection box cover member 58 is pushed between the box opening/closing member 64 and the digging portion 54, and then the cicada loop clamps are hooked into the loops fixedly provided on the both side surfaces of the sample collection box 50, thereby mounting the collection box cover member 58 on the sample collection box 50. With this operation, the collection box cover member 58 is integrated with the sample collection box 50 so that the sample does not flow out even if the sample sampling box 50 is separated from the box-mounting unit 44.

Then, as illustrated in FIG. 10, the crane is lowered to cause the rotary member 62 to rotate downward, and the box opening/closing member 64 to rotate upward. That is, the lifting cable 31 is lowered such that the rotary operation section 60 is placed in a horizontal state.

When the box opening/closing member 64 is released from the lower portion of the sample collection box 50, as illustrated in FIG. 10, the moving carriage 70 is moved to the lower portion of the sample collection box 50, that is, the operating space S, through the opening 24A formed in the frame section 20, the tightening nut 46H of the mounting mechanism 46 is released such that the position-fixing shaft 46D is freely movable in the arc-shaped operation hole 46C, and then the operation bracket 46G is rotated in the direction opposite the engagement direction such that the engagement hook 46E is released from the engagement bar 53.

Through this process, the sample collection box 50 is released from the state of being fixed to the box-mounting unit 44.

Then, the sample collection box 50 is detached from the box-mounting unit 44 by pushing the sample collection box 50 in the direction opposite the direction in which the mounting mechanism 46 is provided, that is, toward the opening 24A.

At this time, both the guide stages 51 of the sample collection box 50 are guided by the guide rails 44A of the box-mounting unit 44 so that the sample collection box 50 is horizontally moved toward the opening 24A to be is seated on the seat portion 74 of the moving carriage 70.

Of course, when the sample collection box 50 is released from the state of being fixed on the box mounting portion 44, the sample collection box 50 is positioned on the moving carriage 70 and the moving carriage 70 is moved to the opening 24A, so that the sample collection box 50 can be easily detached from the box-mounting unit 44.

When the sample collection box 50 is seated on the moving carriage 70, the sample collection box 50 is bound to the moving carriage 70 using the play prevention rope 76 so as to prevent the sample collection box 50 from moving freely while being transported.

When the sample collection box 50 is seated on and bound to the moving carriage 70, the moving carriage 70 is moved to the outside from the operation space S through the opening 24A.

Since the sample collection box 50 detached from the box-mounting unit 44 is horizontally moved, seated on the moving carriage 70, and then moved by the moving carriage 70, the free moving of the sample collection box 50 can be minimized, so that the disturbance of the sample can be prevented.

As described above, in the sample collection apparatus according to the present disclosure, when the frame section 20 is seated on the seabed surface, the sample collection box 50 digs into the sediment and the trigger device 30 is released from its engagement, thereby rotating the rotation operation section 60 such that the box opening/closing member 64 can block the lower portion of the sample collection box 50 to thus prevent the sample from flowing out, and in the state in which the sample collection device is seated on the deck of a ship, the sample collection box 50 filled with the sample can be stably moved without disturbing the sample using the moving carriage 70.

Although the specific embodiment of the present disclosure has been described above, it is apparent to those skilled in the art that the present disclosure is not limited to the embodiment disclosed herein and various modifications and changes can be made without departing from the spirit and scope of the present disclosure. Therefore, such modifications and changes should not be individually construed from the spirit or point of view of the present disclosure, and it should be understood that modified embodiments belong to the claims of the present disclosure.

According to the sample collection apparatus of the present disclosure, the sediment of the sea floor can be stably collected without disturbing the sample by operating the sample collection apparatus with a simple operation, the operation of the sample collection apparatus on a ship can be performed stably since the operation structure of the sample collection apparatus is simple, and the collected sample can be stably transported using a moving carriage. In addition, since the sample collection box is configured to be horizontally movable after being mounted on or detached from the box-mounting unit, the sample collection box can be easily mounted, detached, and transported. Thus, because the present disclosure overcomes the limits of the existing technology, there is a high likelihood that an apparatus to which the present disclosure is applied, as well as an apparatus, which uses the related art of the present disclosure, will become commercially available or operable. Further, it is evident that the present disclosure can be carried out in practice. Thus, the present disclosure is an industrially applicable disclosure.

What is claimed is:

1. A sample collection apparatus comprising:
a frame section having a lower frame seated on a seabed surface and an opening provided at one side thereof, an upper frame connected to the lower frame and having an operation hole formed in a center thereof, and an operation space formed between the upper and lower frames;
a vertical operation section including: a vertical operation member provided through the operation hole to be vertically movable, and including weights provided on left and right sides of a lower portion thereof, and a trigger device provided at an upper end thereof, to be connected to a lifting cable; and a box-mounting unit provided at a lower end of the vertical operation member located in the operation space, and configured such that a sample collection box having opened upper and lower portions is mounted thereon or detached therefrom; and
a rotary operation section having a pair of rotary members coupled to both side surfaces of the box-mounting unit by rotary shafts, wherein one ends of the rotary members are connected to the trigger device by pulling cables and an arc-shaped box opening/closing member is provided at remaining ends of the rotary members, and the rotary operation section is configured such that, after the frame section is seated on the seabed surface, the trigger device is operated, and the vertical operation member descends such that the sample collection box mounted on the box-mounting unit digs into the seabed surface and the rotary members are rotated about the rotary shafts by pulling of the pulling cable such that the box opening/closing member closes the opened lower portion of the sample collection box so as to prevent a sample from flowing out.

2. The sample collection apparatus of claim 1, wherein the trigger device includes:
a lifting connector, of which an upper end is connected to the lifting cable, both ends connected to the pulling cables, respectively, and a lower end is formed with an engagement hole;
a hook member, of which one end is coupled to an inside of the upper end of the vertical operation member by a support shaft and a remaining end is formed with a hook configured to be hooked into the engagement hole; and
a rotation prevention hook member, of which one end is coupled to the support shaft to be rotationally operated together with the hook member within a predetermined angle such that, when the rotary members are rotated upward about the rotary shafts by a pulling operation of the pulling cables, the rotation prevention hook member is engaged with an engagement step provided at one end of the rotary member so as to prevent the rotation of the rotary member,
wherein the hook member is formed at a position shifted to one side such that a vertical center line of the hook is deviated from a vertical center line of the support shaft such that, when the frame section is seated on the seabed surface and the lifting connector, from which tension is removed, descends so that the hook is disengaged from the engagement hole, the hook member is rotated to a direction shifted to one side about the support shaft to be separated from the lifting connector.

3. The sample collection apparatus of claim 2, wherein the trigger device further includes a safety pin passing through an upper end portion of the vertical operation member and the hook, and a pair of guide rollers, which are respectively provided on both side surfaces of upper end portion of the vertical operation member so as to support and guide the pulling cable.

4. The sample collection apparatus according to claim 3, further comprising: a moving carriage configured to horizontally move the sample collection box toward the inside of the box-mounting unit in the state in which the frame section is seated on a ground or on a deck a ship in order to mount the sample collection box on the box-mounting unit, or to move the sample collection box detached from the box-mounting unit.

5. The sample collection apparatus of claim 2, wherein the box-mounting unit is provided with an outflow prevention mechanism configured to prevent the sample from flowing out by covering an opened upper portion of the sample collection box in response to a release operation of the trigger device when the frame section is seated on the seabed surface and the sample collection box digs into the seabed surface,
the outflow prevention mechanism includes:
an upper cover, of which one end is coupled to one side of the bottom surface of the box-mounting unit by a hinge so as to rotate around the hinge to cover the upper portion of the sample collection box; and
an opening/closing wire, of which one end is coupled to the upper cover and a remaining end is connected to a region shifted to one side in a hook member, wherein the opening/closing wire is configured such that, when the hook member is coupled to the lifting connector, the opening/closing wire lifts up the upper cover so as to open the sample collection box, and when the hook member is separated from the lifting connector and is rotated toward the region shifted to one side, the opening/closing wire is relaxed so as to cause the upper cover to rotate by the self-weight thereof and to cover the upper portion of the sample collection box.

6. The sample collection apparatus according to claim 5, further comprising: a moving carriage configured to horizontally move the sample collection box toward the inside of the box-mounting unit in the state in which the frame section is seated on a ground or on a deck a ship in order to mount the sample collection box on the box-mounting unit, or to move the sample collection box detached from the box-mounting unit.

7. The sample collection apparatus of claim 5, wherein in an upper end portion of the vertical operation member, a pair of arc-shaped guide holes is formed to face each other, and in the guide holes, a guide pin, to which the remaining end of the opening/closing wire is connected, is installed through the region shifted to one side in the hook member.

8. The sample collection apparatus according to claim 7, further comprising: a moving carriage configured to horizontally move the sample collection box toward the inside of the box-mounting unit in the state in which the frame section is seated on a ground or on a deck a ship in order to mount the sample collection box on the box-mounting unit, or to move the sample collection box detached from the box-mounting unit.

9. The sample collection apparatus according to claim 2, further comprising: a moving carriage configured to horizontally move the sample collection box toward the inside of the box-mounting unit in the state in which the frame section is seated on a ground or on a deck a ship in order to mount the sample collection box on the box-mounting unit, or to move the sample collection box detached from the box-mounting unit.

10. The sample collection apparatus of claim 1, wherein the box-mounting unit includes a horizontal guide mechanism such that the sample collection box moving in a horizontal direction through the opening is slid to be coupled thereto or detached therefrom, and
the horizontal guide mechanism includes guide rails provided on both sides of the inside of the box-mounting unit to face each other, and guide stages, which are respectively provided on the both side surfaces of the sample collection box, which face the guide rails, to be slidably engaged with the guide rails.

11. The sample collection apparatus according to claim 10, further comprising: a moving carriage configured to horizontally move the sample collection box toward the inside of the box-mounting unit in the state in which the frame section is seated on a ground or on a deck a ship in order to mount the sample collection box on the box-mounting unit, or to move the sample collection box detached from the box-mounting unit.

12. The sample collection apparatus of claim 10, wherein the box-mounting unit is provided with a mounting mechanism configured to fix or release a position of the sample collection box which has entered the inside of the box-mounting unit by the horizontal guide mechanism, and
the mounting mechanism includes:
a pair of support brackets respectively having arc-shaped operation holes on both sides of the inside of the box-mounting unit and coupled to face each other;
an operation bracket, of which one end is formed with an engagement hook opened downward, a middle portion is coupled to the support brackets by a shaft to be rotated by a predetermined angle, and a remaining end is formed with a handle; and
a position-fixing shaft installed through the middle region of the operation bracket, which corresponds to the arc-shaped operation holes, the both ends of the position-fixing shaft being exposed through the arc-shaped holes, and a tightening nut being selectively fastened to each of opposite ends of the position-fixing shaft so as to fix a position of the operation bracket,
wherein, when the sample collection box is made to enter the inside of the box-mounting unit by the horizontal guide mechanism, the operation bracket is rotated such that the engagement hook is engaged with the mounting engagement bar provided on one surface of the sample collection box, and then the tightening nuts are tightened such that the position of the operation bracket is fixed and the sample collection box is mounted on the box-mounting unit.

13. The sample collection apparatus according to claim 12, further comprising: a moving carriage configured to horizontally move the sample collection box toward the inside of the box-mounting unit in the state in which the frame section is seated on a ground or on a deck a ship in order to mount the sample collection box on the box-mounting unit, or to move the sample collection box detached from the box-mounting unit.

14. The sample collection apparatus of claim 1, wherein the sample collection box further includes a collection box cover member, which is configured such that, in a state in which the box opening/closing member closes the lower portion of the sample collection box, the collection box cover member is inserted between the box opening/closing member and the digging portion of the sample collection box to be coupled to the sample collection box while closing the opened lower end of the sample collection box so as to prevent collected sample from flowing out.

15. The sample collection apparatus according to claim 14, further comprising: a moving carriage configured to horizontally move the sample collection box toward the inside of the box-mounting unit in the state in which the frame section is seated on a ground or on a deck a ship in order to mount the sample collection box on the box-mounting unit, or to move the sample collection box detached from the box-mounting unit.

16. The sample collection apparatus of claim 1, wherein a descent prevention mechanism is provided in a lower region of the vertical operation member in order to prevent a descending operation of the vertical operation member in a state in which the frame section is seated on a ground or on a deck of a ship, and
the descent prevention mechanism includes a stop hole formed through the vertical operation member and a stop pin installed through the stop hole in order to prevent descent of the vertical operation member.

17. The sample collection apparatus according to claim 16, further comprising: a moving carriage configured to horizontally move the sample collection box toward the inside of the box-mounting unit in the state in which the frame section is seated on a ground or on a deck a ship in order to mount the sample collection box on the box-mounting unit, or to move the sample collection box detached from the box-mounting unit.

18. The sample collection apparatus according to claim 1, further comprising: a moving carriage configured to horizontally move the sample collection box toward the inside of the box-mounting unit in the state in which the frame section is seated on a ground or on a deck a ship in order to mount the sample collection box on the box-mounting unit, or to move the sample collection box detached from the box-mounting unit.

19. The sample collection apparatus of claim 18, wherein the moving carriage includes a seat portion configured to seat the sample collection box on an upper surface thereof and a play prevention rope configured to fix the sample collection box so as to prevent the sample collection box seated on the seat portion from freely moving while being transported.

* * * * *